United States Patent
Mouris-Laan et al.

[11] Patent Number: 5,882,347
[45] Date of Patent: Mar. 16, 1999

[54] CATHETER WITH INTERNAL STIFFENING RIDGES

[75] Inventors: Judith Alida Maria Petronella Mouris-Laan, Sneek; Lesley Sugito Kasto, Schipborg, both of Netherlands

[73] Assignee: Cordis Europa, N.V., Roden, Netherlands

[21] Appl. No.: 923,031

[22] Filed: Sep. 3, 1997

[30] Foreign Application Priority Data

Sep. 9, 1996 [NL] Netherlands .......................... 1003984

[51] Int. Cl.[6] .................................... A61M 25/00
[52] U.S. Cl. .................... 604/280; 604/96; 604/282; 606/194
[58] Field of Search ................ 604/19, 48, 53, 604/93, 96, 264, 280, 282–284; 606/191, 192, 194

[56] References Cited

U.S. PATENT DOCUMENTS

| | | | |
|---|---|---|---|
| 4,402,684 | 9/1983 | Jessup | 604/264 |
| 4,648,871 | 3/1987 | Jacob | 604/149 |
| 4,790,831 | 12/1988 | Skirbiski | 604/282 |
| 4,846,791 | 7/1989 | Hattler et al. | 604/43 |
| 4,960,410 | 10/1990 | Pinchuk . | |
| 5,019,057 | 5/1991 | Truckai . | |
| 5,037,404 | 8/1991 | Gold et al. . | |
| 5,327,891 | 7/1994 | Rammler | 128/658 |
| 5,337,733 | 8/1994 | Bauerfeind et al. | 128/4 |
| 5,593,394 | 1/1997 | Kanesaka et al. | 604/282 |
| 5,681,296 | 10/1997 | Ishida | 604/282 |

FOREIGN PATENT DOCUMENTS

| | | |
|---|---|---|
| 0454264A1 | 10/1991 | European Pat. Off. . |
| 28 20 239.3-35 | 5/1978 | Germany . |
| 41 13 265.3 | 4/1991 | Germany . |
| 86/00232 | 1/1986 | WIPO . |
| 93/08864 | 5/1993 | WIPO . |

*Primary Examiner*—Corrine M. McDermott
*Assistant Examiner*—Cris L. Rodriguez
*Attorney, Agent, or Firm*—Michael W. Montgomery

[57] ABSTRACT

A medical catheter comprising an outer tubular member and an inner tubular member slidably disposed within a lumen of the outer tubular member. The inner tubular member includes ridges which project outwardly from the outside surface thereof and which extend longitudinally along substantially the entire length of the inner tubular member to thereby provide a catheter which is flexible and highly resistant to kinking. The catheter further includes connectors for coupling the catheter to a source of fluid and for providing a passageway for a guidewire.

7 Claims, 1 Drawing Sheet

CATHETER WITH INTERNAL STIFFENING RIDGES

BACKGROUND AND SUMMARY OF THE INVENTION

The present invention generally relates to a medical catheter, and more particularly, to a catheter that is sufficiently flexible to be guided through a blood vessel and still exhibiting excellent strength and torque response characteristics while being resistant to kinking. The catheter is constructed with a thin flexible outer tubular member which overlies a thin inner tubular member to thereby form the elongated tubular portion of the catheter. The catheter further includes a plurality of longitudinal ridges which extend from the outside wall of the inner tubular member and along the length of the inner tubular member. The inner tubular member with the longitudinal ridges is dimentioned to be slidably received in the lumen of the outer tubular member to thereby prevent kinking of the catheter during use.

Catheters, such as angiographic or angioplasty catheters, are well known for use in diagnostic and therapeutic applications wherein it is necessary to administer a fluid to, or otherwise reach, a precise location within the cardiovascular system of a human body. Such catheter function by guiding the tip or distal end of the catheter through branching blood vessels. Such guiding is accomplished in part by manipulation of a proximal portion of the catheter in order to impart the forces needed to curve and guide the catheter through curving and branching blood vessels.

In view of the fact that these types of catheters are used in a vascular environment, the catheter must have an extremely small outside diameter. Inasmuch as such catheters typically come into contact with living tissue, including blood vessels and organs such as the heart, it is extremely important that the catheter be in place for a minimal length of time. The overall insertion time includes the length of time needed to transmit the therapeutic or diagnostic fluid through the length of the catheter. This flow velocity is dependent upon the internal diameter of the catheter, as well as the strength of the catheter. Catheter strength is a limiting factor to the pressure which can be applied in order to transmit the fluid therethrough. It is also important that these catheters be very resistant to the formation of kinks which requires a certain degree of stiffness, while at the same time possessing adequate flexibility to be responsive to maneuvering forces. These catheters must also be sufficiently flexible to be as atraumatic as possible. Catheters which require a relatively stiff, but flexible, body portion must have these properties. Included are intravascular catheters, guiding catheters through which balloon catheters for angioplasty techniques and the like can be passed, balloon catheters and sheaths.

The present invention provides a medical catheter having a proximal end and a distal end adapted to be guided through blood vessels. The catheter includes an elongated, outer tubular member extending over the length of the catheter. The outer tubular member has an inner lumen. An elongated inner tubular member is disposed within the lumen of the outer tubular member and is substantially co-axial with the outer tubular member. The inner tubular member has a plurality of longitudinal ridges projecting outwardly from its outer surface and the longitudinal ridges extend along substantially the entire length of said inner tubular member. The inner tubular member also has an inner lumen and is free to slide or move over substantially its entire length within the inner lumen of the outer tubular member. A first fluid connector member is coupled to the proximal end of the catheter and has a passageway which communicates with the lumen of the inner tubular member, and a second fluid connector is coupled to the proximal end of the catheter and has a passageway which communicates with a lumen defined between the inside wall of the outer tubular member and the outside wall of the inner tubular member. Accordingly, the resulting catheter is extremely flexible while being highly resistant to kinking.

There is also provided a catheter as described above in which the outermost surface of each of the ridges is arcuate in shape with a radius of curvature equal to approximately the same radius of curvature of the inner lumen of the outer tubular member. The medical catheter preferably includes three longitudinal ridges, or any odd number of ridges other than one, which are evenly spaced around the circumference of the outer surface of the inner tubular member.

There is also provided a medical catheter of the type described above in which an inflatable balloon member is mounted on the outside surface of the outer tubular member at the distal end of the catheter and is sealed to the outside surface at both ends of the balloon. The outer tubular member has at least one passageway extending through the wall thereof which communicates with the interior of the inflatable balloon so that the balloon may be inflated by the application of a fluid pressure to the second fluid connector.

By this combination, it has been discovered that the advantages of a catheter having internal stiffening are achieved while at the same time providing a catheter that has the thin-walled properties often associated with catheters having single-layered walls, including the atraumatic and flexibility attributes normally associated therewith, however, being highly resistant to kinking.

Accordingly, a general object of the present invention is to provide a thin-walled flexible catheter which is highly resistant to kinking.

Another object of the present invention is to provide a thin-walled flexible catheter that is particularly suitable for delicate medical treatments and diagnostic procedures, including angiography and angioplasty, and other similar procedures which are performed within the vascular system.

Another object of the present invention is to provide an improved thin-walled catheter that has an inner tubular member having spaced ridges and an outer tubular member in which the tubular members are free to move relative to each other over most of the length of the members to thereby provide a very flexible catheter.

Another object of the present invention is to provide an improved intravascular catheter which exhibits excellent torque response, or control, and which is particularly resistant to kinking, while still possessing the flexibility and atraumatic properties needed for an intravascular catheter.

These and other objects, features and advantages of the present invention will be clearly understood through a consideration of the following detailed description.

BRIEF DESCRIPTION OF THE DRAWINGS

In the course of this description, reference will be made to the attached drawings, wherein.

DESCRIPTION OF A PREFERRED EMBODIMENT

Figure 1:
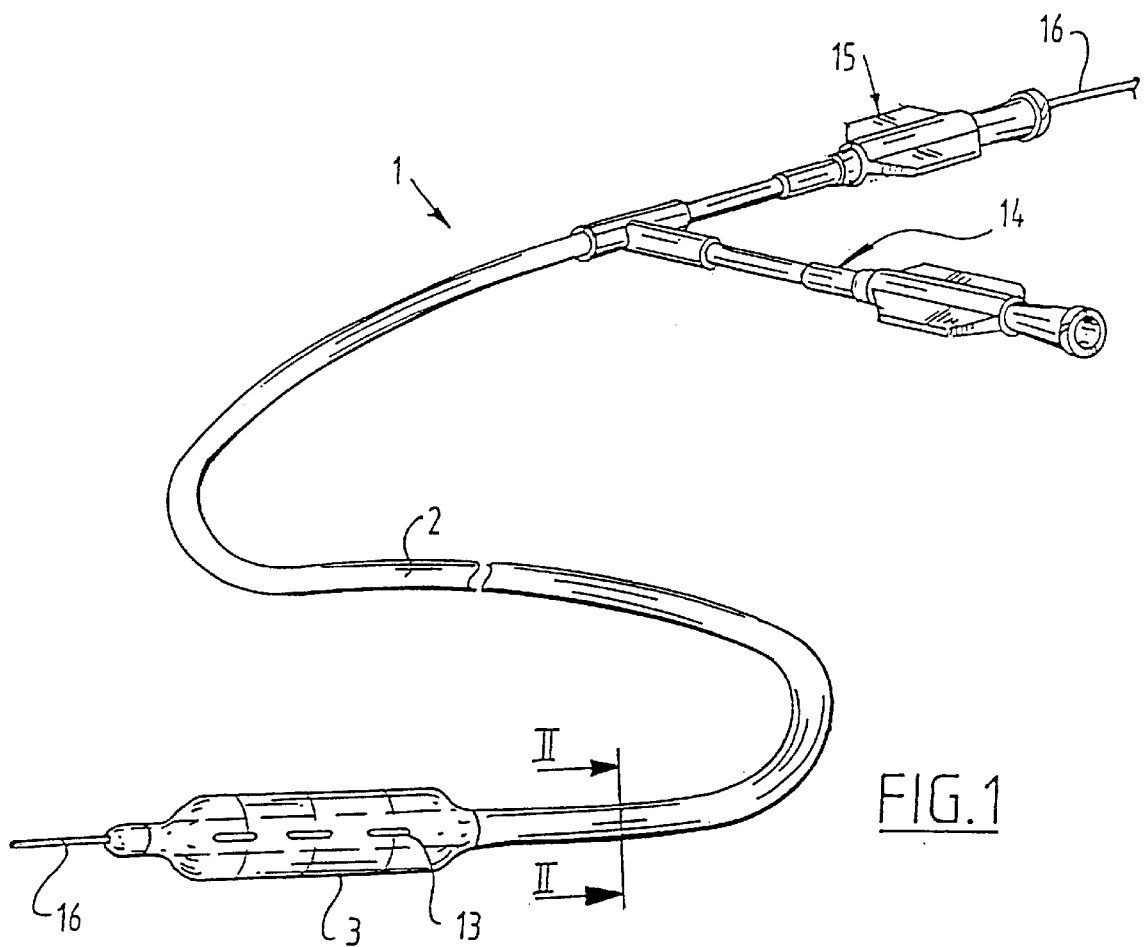
FIG. 1 illustrates a perspective view of a balloon catheter according to the invention; and, FIG. 2 illustrates in perspective view a cross-section taken along the line II—II of FIG. 1.

As illustrated in FIG. 1, a balloon catheter 1 includes a tubular outer body 2 a balloon member 3 attached to the distal end thereof. The proximal end of the tubular body 2 has been connected to connecting members 14, 15, for coupling the balloon catheter to a source of fluid for permitting the insertion of a guidewire into the balloon catheter.

Figure 2:
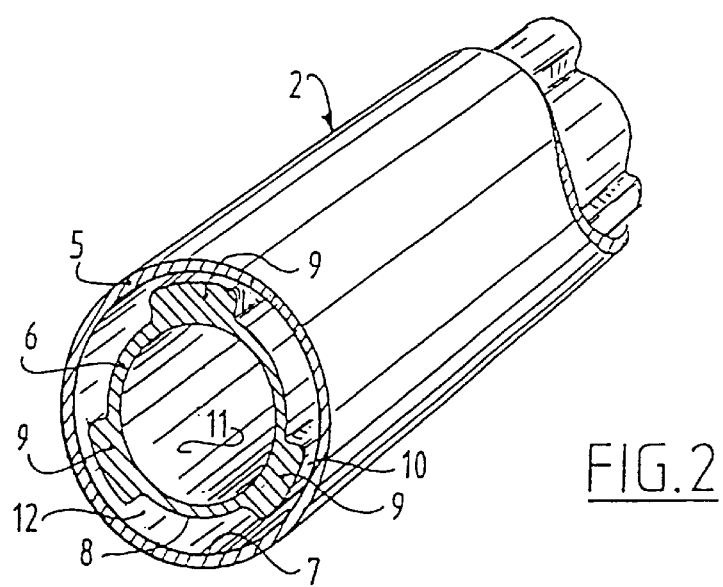

As shown in FIG. 2, the basic tubular outer body 2 has been formed by a first tube-like element 5 with a lumen 12 which is bounded by a lumen wall 7. A tubular inner body element 6 is disposed inside the lumen 12. The tubular inner body includes a lumen 11.

The outer wall 8 of the tubular inner body 6 has been provided with ridges 9 which extend in the longitudinal direction of the tubular outer body 2. The ridges 9 reinforce the tubular inner body 6 to such an extent that it becomes essentially kink resistant.

Upon bending the tubular outer body 2 rather sharply, the lumen wall 7 will be positioned against the top-surfaces 10 of the ridges 9 due to a flattening of the cross-section of the first tube-like element 5. On the one hand the tubular inner body 6 is supported as a result, so that it can be bent more sharply before it buckles. On the other hand, the first tube-like element 5 is supported internally by the ridges 9, so that this first tube-like element 5 is more resistant to buckling. The result of these effects is that the tubular outer body 2 of the catheter 1 displays a significant resistance to buckling.

As shown in FIG. 2, the top-surfaces 10 of the ridges 9 are substantially concentric with the tubular inner body 6 and consequently with the tube-like element 5, so that these top-surfaces 10 make contact with the lumen wall 7 in an even fashion. Upon making contact no concentrations of stress will occur in the wall of the first tube-like element 5, which is desirable in order to prevent buckling.

The function of the central lumen 11 in the second tube-like element 6 of catheter 1 is to provide a passage for a guidewire 16.

During an angiographic procedure a guidewire is introduced into a patient after which the catheter 1 is passed over the guidewire 16 into the body of the patient until the balloon member 3 has arrived in the target position. The tubular outer body 6 extends over the entire length of the catheter and the lumen 11 is accessible byway of the connecting member 15 at the proximal end of the catheter.

The remaining space of the lumen 12 of the first tube-like element 5 has been made accessible by way of a connecting member 14 of which a channel is connected to this lumen 12 through an opening in the wall of the first tube-like element 5. At the distal end of the catheter a number of openings 13 have been arranged in the wall of the first tube-like element 5 at the site of the balloon member 3, so that the lumen 12 is connected with the inside of the balloon member 3 through these openings 13. By introducing fluid under pressure into the balloon member 3 and through the connecting member 14, the balloon member 3 may be expanded in order to carry out an angioplasty procedure.

Although the ridges 9 have been arranged on the outer wall of the second, tubular inner body 6, it is also possible to provide the ridges on the inside, or on the lumen wall 7. These ridges will reinforce in that case the tubular outer body 2 due to the cooperation with the tubular inner body 2 as described above, therefore, the entire catheter 1 becomes kink resistant.

The number of ridges 9 shown are three, and the ridges have been arranged evenly distributed around the circumference. Other numbers of ridges are possible.

It will be understood that the embodiments of the present invention which have been described are merely illustrative of a few of the applications of the principles of the present invention. Numerous modifications may be made by those skilled in the art without departing from the true spirit and scope of the invention.

That which is claimed is:

1. A medical catheter having a proximal end and a distal end adapted to be guided through a blood vessel, comprising:

an elongated, outer tubular member, said outer tubular member having an inner lumen; plan elongated inner tubular member disposed within the outer tubular member and being substantially co-axial with an outer tubular member, said inner tubular member having a plurality of longitudinal ridges projecting outwardly from the outer surface of the inner tubular member and extending along substantially the entire length of said inner tubular member, said inner tubular member having an inner lumen, and said inner tubular member being free to slide over substantially all of its length within the inner lumen of the outer tubular member;

a first fluid connector member coupled to the proximal end of the catheter and having a passageway which communicates with the lumen of the inner tubular member; and, a second fluid connector coupled to the proximal end of the catheter and having a passageway which communicates with a lumen defined between the inside wall of the outer tubular member and the outside wall of the inner tubular member to thereby provide a catheter which is flexible while resistant to kinking.

2. The medical catheter as defined in claim 1, wherein the outermost surface of each of the plurality of longitudinal ridges is arcuate in shape with a radius of curvature equal to approximately the same radius of curvature of the inner lumen of the outer tubular member.

3. The medical catheter as defined in claim 2, wherein said longitudinal ridges are three in number, and said three longitudinal ridges are evenly spaced around the circumference of the outer surface of the inner tubular member.

4. The medical catheter as defined in claim 2, wherein the number of the plurality of longitudinal ridges is an odd number.

5. The medical catheter as defined in claim 2, which includes an inflatable balloon member mounted on the outside surface of the outer tubular member at the distal end of the catheter and being sealed to the outside surface at both ends of the balloon; and, said outer tubular member having at least one passageway extending through the wall thereof and communicating with the interior of the inflatable balloon so that the balloon may be inflated by the application of a fluid pressure to the second fluid connector.

6. The medical catheter as defined in claim 5, wherein said longitudinal ridges are three in number, and said three longitudinal ridges are evenly spaced around the circumference of the outer surface of the inner tubular member.

7. The medical catheter as defined in claim 5, wherein the number of the plurality of longitudinal ridges is an odd number.

* * * * *